(12) United States Patent
Price et al.

(10) Patent No.: US 7,040,885 B2
(45) Date of Patent: May 9, 2006

(54) DUPLICATION OF LOST DENTURES

(76) Inventors: William Raymond Price, 1452 Ridgemere La., Winston-Salem, NC (US) 27106; Cannon Gary Sample, 229 Brittany Joy Dr., Winston-Salem, NC (US) 27107

( * ) Notice: Subject to any disclaimer, the term of this patent is extended or adjusted under 35 U.S.C. 154(b) by 243 days.

(21) Appl. No.: 10/654,166

(22) Filed: Sep. 3, 2003

(65) Prior Publication Data

US 2004/0043093 A1    Mar. 4, 2004

Related U.S. Application Data

(62) Division of application No. 10/035,885, filed on Dec. 24, 2001, now Pat. No. 6,730,246.

(60) Provisional application No. 60/288,513, filed on May 3, 2001, provisional application No. 60/288,515, filed on May 3, 2001.

(51) Int. Cl.
    *A61C 13/10*    (2006.01)
(52) U.S. Cl. ............... 425/176; 425/178; 425/DIG. 44; 433/167; 433/171

(58) Field of Classification Search ........ 425/DIG. 44, 425/175, 176, 178; 433/167, 171
See application file for complete search history.

(56) References Cited

U.S. PATENT DOCUMENTS

| | | | | |
|---|---|---|---|---|
| 4,195,047 A | * | 3/1980 | Drennan et al. | ............... 264/17 |
| 4,521,193 A | * | 6/1985 | Cialone | ................... 433/199.1 |
| 5,151,279 A | * | 9/1992 | Kimura | ...................... 425/178 |
| 5,324,186 A | * | 6/1994 | Bakanowski | ................. 425/116 |
| 5,599,491 A | * | 2/1997 | Pollock et al. | ............... 264/138 |
| 6,224,375 B1 | * | 5/2001 | Diasti et al. | ................. 433/213 |

* cited by examiner

*Primary Examiner*—Joseph S. Del Sole
(74) *Attorney, Agent, or Firm*—Robert W. Pitts

(57) ABSTRACT

A mold used in duplicating a denture consists of a tissue side mold section and an exterior side mold section. The tissue side mold section is made of a dimensionally stable material, such as dental stone or an addition-cured silicone rubber, so that the tissue side of the denture can be accurately reproduced at a later time. The exterior side mold is made of a resilient material, so that the original denture and its duplicate can be removed from the mold. The mold sections are housed in a two part flask that was initially used to fabricate the mold sections. The mold is fabricated by the steps of forming an impression of the original denture, and of fabricating a replacement denture using this mold.

15 Claims, 12 Drawing Sheets

DUPLICATION OF LOST DENTURES

CROSS REFERENCE TO CO-PENDING PATENT APPLICATIONS

This is a divisional of application Ser. No. 10/035,885 filed Dec. 24, 2001, now U.S. Pat. No. 6,730,246, which application claims the benefit of previously filed, now abandoned Provisional Patent Application Ser. No. 60/288,513 filed on May 3, 2001 and also of Provisional Patent Application Ser. No. 60/288,515 filed on May 3, 2001.

BACKGROUND OF THE INVENTION

1. Field of the Invention

This invention is related to an apparatus and method for producing a denture that is a duplicate of an original denture, and can be provided to a denture wearer when the original denture is lost. The invention also relates to the fabrication of a mold that conforms to the shape of the original denture.

2. Description of the Prior Art

Several patents discuss situations in which copies of dentures may be desirable and disclose methods of making those denture copies. It has been suggested that a temporary denture can be fabricated in a dentist's office so that the denture wearer will have a temporary denture to use while the dentist makes repairs to the original denture. It has also been suggested that a replacement denture can be fabricated using a indexed impression of a worn denture. It has also been suggested that denture wearers may require at least one identical denture in case of loss, breakage or repair of the original denture.

U.S. Pat. No. 4,521,193 discloses one method of making a temporary denture in which an impression is first made of the outer surfaces of the denture wearer's permanent denture. A molding material, such as an irreversible hydrocoloid, for example alginate, is mixed with water to form a colloidal suspension and placed in a molding shell. The permanent denture is then placed in the molding material to form an impression of the exterior surfaces of the permanent denture. The permanent denture is then removed and the molding material is allowed to set. A polymerizable liquid acrylic material with tooth colored powder is then placed in the tooth area of the impression. Methylmethacrylate is a suitable dental acrylic that can be used to form a portion of this temporary denture. The remaining surface of the impression is then covered with a pink colored acrylic to form a layer, slightly thinner than the permanent denture. The acrylic is then cured forming an acrylic shell. A soft denture liner is then placed on the inside portion of this acrylic shell. The shell and inner liner are then placed in the denture wearer's mouth. After the liner has set, the temporary denture is removed and trimmed. This method requires the assistance of the denture wearer, which may not be possible if the patient is elderly or suffers from dementia. This method is also primarily intended to provide a temporary denture that is suitable for short term use, while a permanent denture is repaired or replaced.

U.S. Pat. No. 5,711,668 discloses a method in which an impression mold of a worn denture is made by embedding the worn denture in an impressionable material, such as alginate, in a two part dental flask. The worn denture is removed and the impression mold is filled with methyl methylmethhacrylate, or a similar material, to form a stint that replicates the original denture. Adjustments or modifications can then be made to the stint. For example, the proper bite opening can be restored or the dentures can be modified to properly center the upper and lower jaw, by using bite material impressions. A two layered model is then obtained by filling undercuts in the stint with a resilient material, and clipping these resilient layers to a rigid layer formed by dental stone or gypsum poured onto the resilient layer. The resilient layer permits removal of the stint from the two layered model. The stint and the two layered model are mounted in an articulator and modifications are made to insure proper vertical positioning and centering. The stint is removed and the two layered model is used to construct a baseplate corresponding to soft tissue surfaces and teeth are set according to information gathered in a wax wafer, and wax try-in is conducted. Dental stone is then poured into the baseplate, after which a new denture is finished using standard processing techniques. Although this technique allows useful information to be gathered from an older worn denture, it does not provide a means for duplicating a denture or quickly replacing a lost denture. The production of a new denture by this method would appear to require considerable time and effort on the part of the dentist or a dental technician. This method instead is directed to the use of a mold and stint derived from an original denture to obtain information useful for the fabrication of a new denture that may or may not be identical to the original denture.

U.S. Pat. No. 5,607,628 discloses a method of making a copy of a denture in which the gum portion of a denture is embedded up to the lower level of the teeth in a dental molding material, such as hard plaster, to form a mold. Before the hard plaster completely hardens, excess plaster is removed to free the denture. The mold is then placed in a lower portion of a flask and is fixed by surrounding it with a plaster of medium hardness. A polymerizable resin material, such as a silicone resin, is then poured over the tooth portion of the denture to form a mold for the tooth portion. The upper part of the flask is filled with medium hard plaster and the flask is placed in a dental type press. After the plaster hardens, the mold surrounding the teeth is removed and a polymethylmethacrylate is deposited in this half of the mold to form the teeth. The teeth are then removed, individually separated and individually trimmed. The individual teeth are then repositioned in the mold. A resin suitable for forming the gum base is then deposited in the other mold and in the remaining space in the tooth mold in an operation know as wedging, and the two halves of the flask are closed an locked in a hydraulic press. This prior art method does not however appear to use a dimensionally stable material only to make a mold or impression of only the tissue side of a denture while using a resilient or more deformable material to make a mold or impression of the remainder of the denture.

The loss of dentures by the elderly, especially by those who suffer from some degree of dementia, is a problem for several reasons. In many cases the elderly denture wearer cannot provide the assistance to and interaction with a dentist who is attempting to make a replacement denture. Properly fitting dentures are thus difficult and/or expensive to fabricate. Indeed dental care for the elderly is a difficult task for the dentist and dental professional. For that reason, the dental care needs of the elderly may not be adequately served. Poor dental health, especially for the elderly, can lead to other problems, such as poor nutrition. The loss of dentures by the elderly is a particular problem in long term health care facilities. When an elderly denture wearer loses his or her dentures, it becomes difficult for them to eat properly, and in long term health care facilities in often becomes necessary to provide specially processed foods for that person. Of course, this increases the cost of health care and can be frustrating to that person's relatives. This problem leads to additional friction between those caring for the elderly resident of rest and nursing homes.

If a simple means of promptly replacing a lost denture were available, the problems of adequately caring for the elderly would be somewhat alleviated. A duplicate denture, that would be less expensive than a new denture, would be at least a partial solution to this problem. However, the new denture would have to fit properly, without extensive custom fitting, and it would often be necessary to fabricate the duplicate denture many years after construction of the original denture. Thus a mold of the original denture, fabricated at the time that the original denture was constructed, would need to be suitable for use many years later. The instant invention provides a mold and a method that could be used to fabricate a duplicate, properly fitting, denture, many years after construction of the original denture. This new mold uses a rigid, dimensionally stable material to form an impression of critical areas of the denture, and a more flexible material to form an impression of other areas of the denture where small variations would be less likely to cause discomfort when the duplicate denture is in use. The flexible material also facilitates removal of both the original and the duplicate denture from the mold without damage.

SUMMARY OF THE INVENTION

According to this invention, a method of supplying a replacement denture to a denture wearer upon the loss of an original denture, without requiring the assistance of the denture wearer to fit the replacement denture includes the following steps. A mold is formed by depositing a material in surrounding relationship to the original denture before the material takes a substantially permanent set. The material is allowed to take on a substantially permanent set. The original denture is then removed from the mold. The mold is then stored with the mold retaining its substantially permanent set configuration. When a replacement denture is subsequently needed the mold is removed from storage and an initially fluent denture material is introduced into the mold and the denture material is then allowed to solidify within the mold. The replacement denture is then removed from the mold and its exterior shape will be substantially to the exterior shape of the original denture, which was fabricated many years previously.

BRIEF DESCRIPTION OF THE DRAWINGS

FIG. 13 is a three dimensional view of a subassembly including an original denture and a temporary sacrificial or filler member formed of a malleable material that is mounted on the inside of a flask cover.

FIG. 14 shows the manner in which an exterior side mold is fabricated according to this second embodiment, in Which the subassembly shown in FIG. 13 is mounted to a flask base and a fluid curable material is poured into tile dental flask.

FIG. 15 is a top view of the exterior side mold part fabricated by allowing the material poured into the flask to cure or set as a flexible solid member.

FIG. 16 is a top view of the flask cover showing a central hole or opening through which a curable fluid is poured to form the tissue side mold half.

FIG. 17 shows the step of pouring the fluid material through the opening in the flask cover into contact with the exposed tissue side of the original denture so that a flexible tissue side mold part can be fabricated.

FIG. 18 is a view of the tissue side mold formed by allowing tile fluid material to cure or set as a flexible, solid member.

FIG. 19 is a view of the mated tissue side mold and exterior side mold with a mold cavity formed after removal of the original denture.

FIG. 20 shows a subassembly consisting of an original denture mounted on a temporary filler or sacrificial material that is mounted in a tray which simplifies fabrication of this subassembly.

FIG. 21 is a view of the tray used in FIG. 20.

DETAILED DESCRIPTION OF THE PREFERRED EMBODIMENT

Figure 1A:
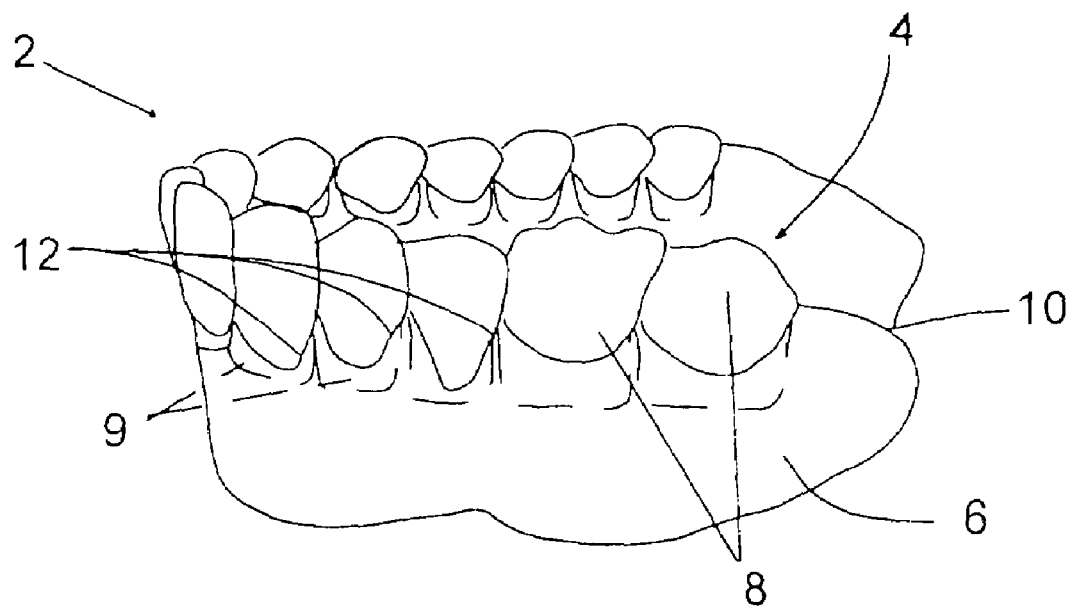
FIG. 1 is a three dimensional view of a maxillary or upper denture that can be duplicated using the method and apparatus of the preferred embodiment.
Figure 1B:
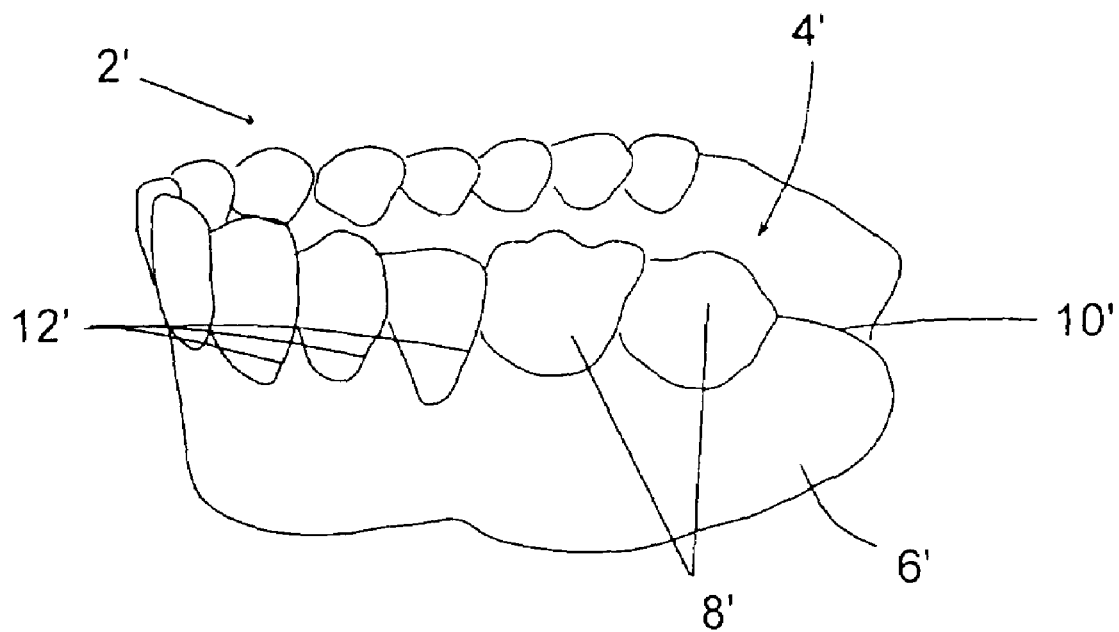

The maxillary or upper dentures 2 and 2' shown in FIGS. 1A and 1B represent respectively an original denture 2 and the duplicate or clone or replacement 2' of that denture that can be fabricated using the method of the instant invention. Although the representative embodiment of the embodiment is described with reference to a maxillary or upper denture, it should be understood that the same method could be used to duplicate or replicate a mandibular or lower denture. Although this method is of particular value in replacing a lost denture, it should also be understood that it could also be used to fabricate a second, relatively more inexpensive, denture, at the time an original denture is fabricated.

Figure 2:
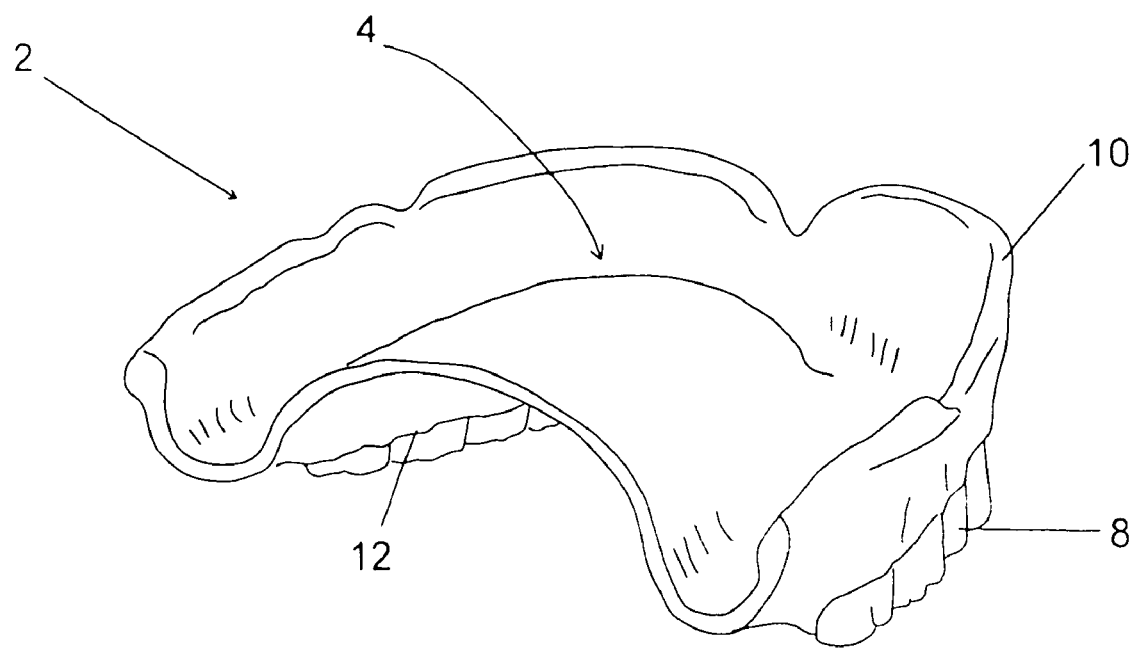
FIG. 2 is a view of the tissue side of the maxillary denture shown in FIG. 1.

Denture 2, shown in FIG. 1A, is a conventional denture fabricated under the supervision of a licensed dentist according to standard dental practices. This maxillary denture has a tissue side 4 along the top surface of the denture. This tissue side 4 is the part of the denture that will be in contact with the denture wearer's tissue and will be supported by this denture wearer's mouth. The tissue side 4 of an upper denture is shown in more detail in FIG. 2. If this tissue side 4 does not fit properly, the denture wearer may feel pain or irritation and sore spots may develop on the denture wearer's mouth. It is therefore important that the duplicate denture, created using this method, have the same tissue side shape as the original denture that was properly fitted by a dentist. The exterior side 6 of the denture 2 should also conform as near as possible to the shape of the original denture, but the dimensional tolerances for the exterior denture side 6 are not as critical as for the tissue side 4. The exterior side 4 includes the entire outer surface of the teeth 8 and that portion of the gum 10 that is not located on the tissue side 4. A gum line 12 is formed between the teeth 8, which are white in color and the pink gum section 10 of the denture 2. The denture 2, shown in FIG. 1A includes individual teeth 8 that are set in the material forming the gum portion 10 of the denture. The teeth 8 include root sections 9, shown in phantom in FIG. 1A, and these root sections extend into the gum portion 10. The duplicate or replacement denture 2', shown in FIG. 1B, has the same exterior shape as the original denture 2, but the denture 2' does not include individual teeth 8 or root sections 9 extending into the gum. The teeth 8' have a white pigment and are separated from the pink gum portion 6' by the gum line 12, but the exterior contour 4' of the entire replacement or duplicate denture 2' will substantially conform to the exterior contour 4 of the original denture 2.

In order to duplicate an original denture 2, a mold 20 will be created by using the original denture to form an upper mold section 24, conforming to the tissue side 4 of the original denture 2, and a lower mold section 32, which will conform to the exterior portions of the original denture. In other words, the second mold section 32 will conform to all remaining portions of the original denture 2, except the denture tissue side 4, to which the tissue side mold section 30 is matched.

Figure 3:
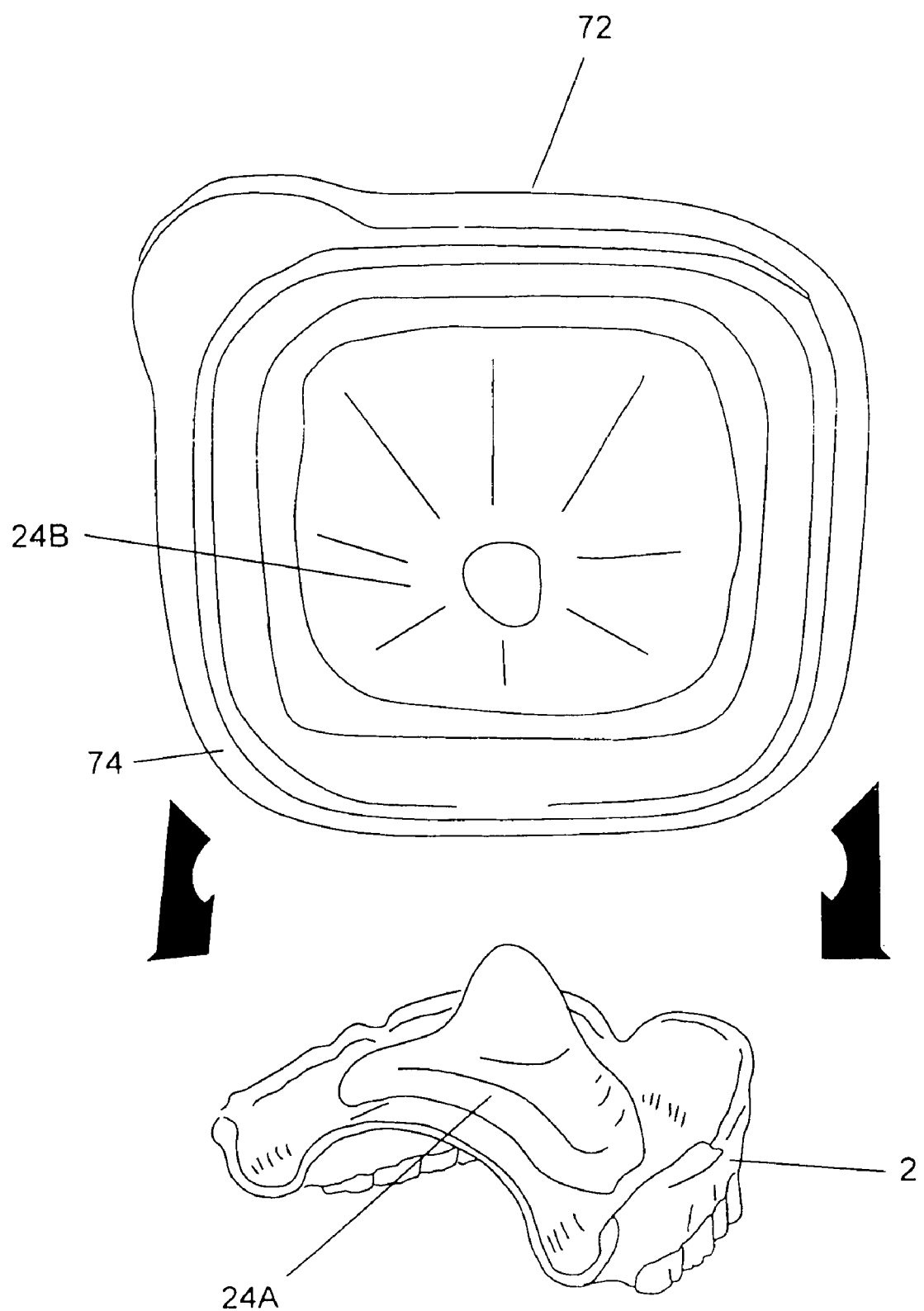
FIG. 3 is a view showing the application of a slurry to the tissue side of a maxillary denture and the inner surface of a dental flask lid. This paste will solidify to form a dimensionally stable mold section that can be used to mold the tissue side of a duplicate denture.

To fabricate the tissue side mold section 24, the tissue side 4 of the original denture 2 is first coated with a releasing agent that will allow separation of the denture 2 from the mold section that will conform to the tissue side 4. Petroleum jelly is one suitable releasing agent. After the releasing agent has been applied, a dental stone slurry or mixture is then applied to the tissue side 4 of the original denture 2. This slurry or paste is applied to the tissue side 4 as shown in FIG. 3. This material can be applied with a spatula or suitable dental tool. Note that that the material is not applied on the exterior of the original denture or on any surface that would not come into contact with the denture wearer's mouth when the denture 2 is in use. FIG. 3 shows only a partial application of the slurry or paste to the tissue side 4. When finished, the entire tissue side will be covered with this material.

FIG. 3 also shows that the material applied to the denture tissue side 4 forms only a part of the first or tissue side mold section 24. The second portion of this mold section 24 is formed by covering the inner surface 74 of a dental flask lid or cover 72 with the same slurry or paste material. Preferably the slurry or paste is applied to both surfaces at the same time. When the slurry or paste has been applied to both the denture tissue side 4 and to the lid 72, the two portions lid 72, with the slurry or paste applied in a procedure commonly referred to as "cow piling", is then mated or joined to the mass of material placed on the denture tissue side 4. These two portions are joined before the slurry or paste has had time to set or form a permanent, rigid or dimensionally stable structure. In the preferred embodiment of this invention the slurry or paste that is applied to the tissue side 4, and forms the tissue side mold section 24 is dental stone. This plaster or gypsum type material is commonly used in dental procedures, and when the dental stone is allowed to set up or dry, it will form a relatively rigid structure that is permanent and will remain dimensionally stable for a period, at least equal to the intended life of an original denture. The dental stone will conform to the tissue side surface so that it can be used to accurately replicate the tissue side 4 of an original denture 2. Therefore a duplicate denture, fabricated using this dental stone mold section 24 will conform to or fit the load bearing and support surfaces of a denture wearer's mouth as closely as would the original denture. Furthermore, this dental stone mold section 24 will retain its shape and be dimensionally stable for at least as long as the anticipated life of the original denture. This mold section can then be used to replicate the original denture if it is lost or damaged many years after fabrication of the original denture and/or fabrication of the dental stone mold section 24. Another advantage of using dental stone on only the tissue side 4 of the denture 2 is that this part of the denture will not have undercuts that will prevent removal of the original denture after the dental stone has hardened or has set up. It is for this reason that the dental stone is applied to the tissue side only of the original denture during fabrication of the first mold section 24. Although dental stone is used in the preferred embodiment of this invention, other materials can be used to form the tissue side mold section 24, if that alternative material possesses sufficient dimensional stability to permit duplication of the tissue side 4 of the denture 2 with sufficiently tight tolerances that the duplicate denture will fit a denture wearer's mouth in substantially the same manner as the original denture 2.

The tissue side mold section 24 will have two surfaces. The first or interior mold surface will be a mold contour surface 28 that conforms to the denture tissue side 4. The second or outer mold surface 26 will conform to the inner surface 74 of the dental flask lid 72. This inner lid surface 74 includes registration indicia or marks 78. Since the mold outer surface 26 will conform to the lid inner surface 74, mold registration marks or indicia 30 will be formed on the exterior surface of the mold section 24. These companion registration marks 30, 78 will permit alignment of the mold section 24 with the lid 72, so that the mold section 24 can be properly positioned in a dental flask 60 when the lid 72 is mated to the dental flask base 62.

Figure 4:
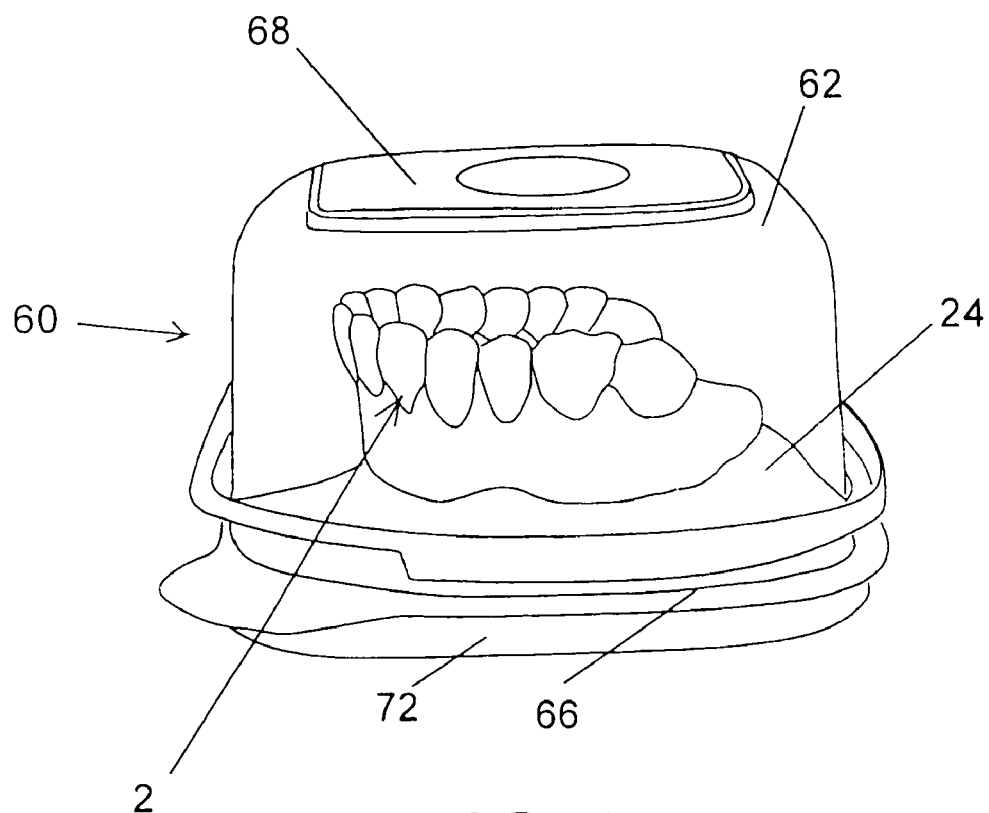
FIG. 4 is a view showing the original denture and the tissue side mold mounted in a dental flask having a base to which a lid is mated.
Figure 5A:
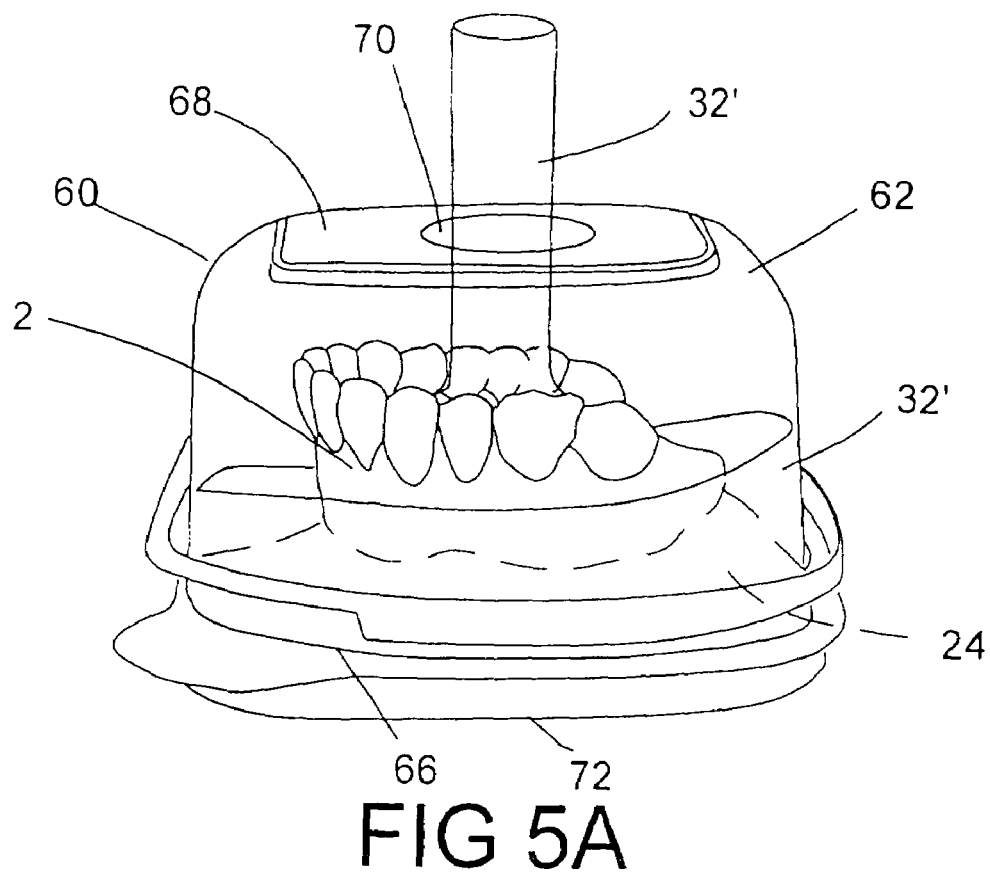
FIG. 5 is a view of a step in which a curable liquid is poured into the dental flask to form the remainder of the mold surrounding the original denture.
Figure 5B:
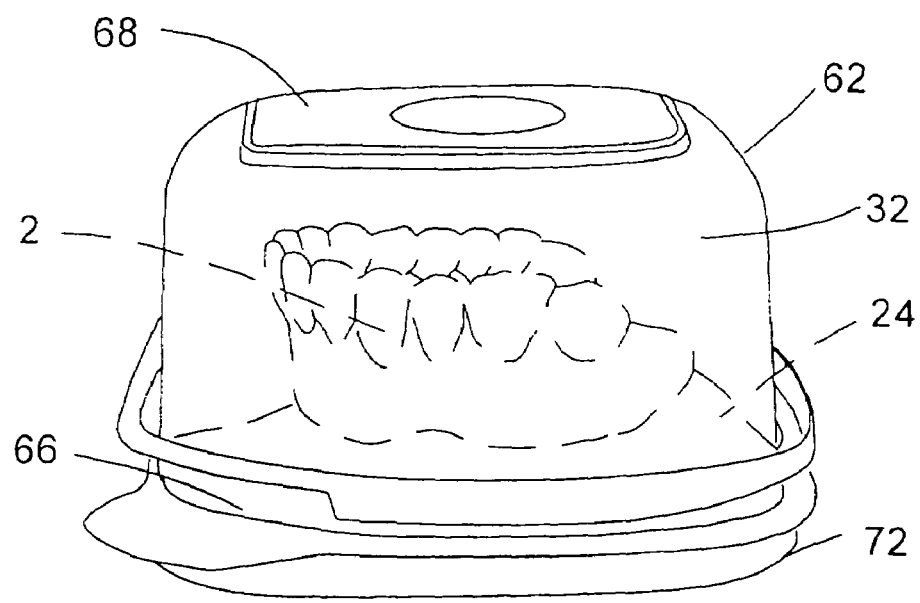

The second or exterior side mold section 32 is fabricated in the dental flask 60. With the original denture 2 still mounted on the tissue side mold section 24, and with the mold section 24 registered and aligned with the lid 72, the dental flask base 62 is mated with the lid 72. In the preferred embodiment of this invention, both the lid 72 and the dental flask base 60 are fabricated from an injection molded plastic, so that the flask is relatively inexpensive and so that the mold sections and the flask together form a dedicated mold assembly for each duplicate denture. The base 62 has four side walls 64 which form a peripheral lip 66 that fits within a groove 76 on the lid 72. When the lid 72 is attached to the base 62, as shown in FIG. 4, the denture 2 and the tissue side mold section 24 will be located on the interior of the dental flask 60. The base 62 has a bottom wall 68 that has at least one opening or hole 70 through which a liquid polymer or other curable material can be injected or poured into the dental flask 60 as shown in FIG. 5. In the preferred embodiment a polymer, such as a polyvinyl rubber is used to form the second solid part of the mold 20 or to from the exterior side mold section 32. When a liquid polymer is poured into the flask 60 in this manner, this liquid will cover all remaining exterior surfaces of the original denture 2, and this liquid will also abut all exposed surfaces on the first mold section 24. The parting line between the two mold sections 24, 32 will be along the edge of the tissue side of the denture, which is also the edge of the portion of the denture that will be in contact with the denture wearer's gums. The original denture 2 will then be completely enclosed by the two mold sections 24, 32 after the liquid polymer has cured or set up. The polyvinyl rubber or similar material or resin that is used to form the exterior side mold section 32 will conform to the teeth 8, the gum 10 and the gum line 12 of the original denture 2, and it will form an impression or contour having substantially the same shape as the original denture 2, after the polymer has cured and solidified. However, the resiliency, elasticity, or flexibility of this portion of the mold will allow deformation of portions of the exterior side mold section 32 to allow removal of original and duplicate dentures. The resilient material will return to its shape after removal of either the original or new duplicate of the original denture.

The exterior side mold section 32 is formed from a material that is more flexible, resilient or elastic than the dental stone used to form the tissue side mold section 24. The exterior surface of a denture, including the teeth, the gum line and the exterior portions of the gum need not fit tightly to the denture wearer's gum or other surfaces of the denture wearer's mouth that will support the denture or bear loads transferred through the denture to the denture's wearer's oral cavity. Therefore the fit is not as critical for those portions of the denture as on the tissue side of the denture. However, those exterior surfaces of the denture will normally include undercuts, which would make it difficult to remove either the original denture or the duplicate denture from the mold, if the exterior side mold 32 were fabricated of a relatively rigid material, such as dental stone. Therefore by fabricating the more dimensionally critical tissue side mold section 24 from a dimensionally stable material, such as dental stone, and by fabricating the exterior side mold section 32 from a more resilient material, such as polyvinyl rubber, the original or duplicate dentures can be removed from the mold, and the tissue side of the new denture will fit properly when used by the denture wearer.

Figure 7:
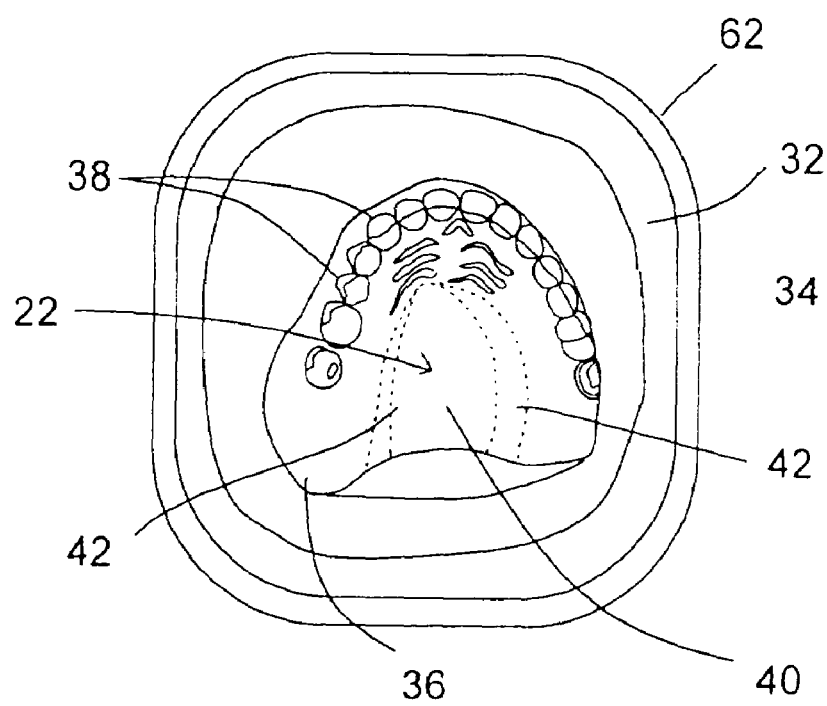
FIG. 7 is a view of the portion of the mold that conforms to the teeth or exterior side of the mold, after this portion of the mold has solidified to form a relatively flexible body that permits removal of the original denture.
Figure 8:
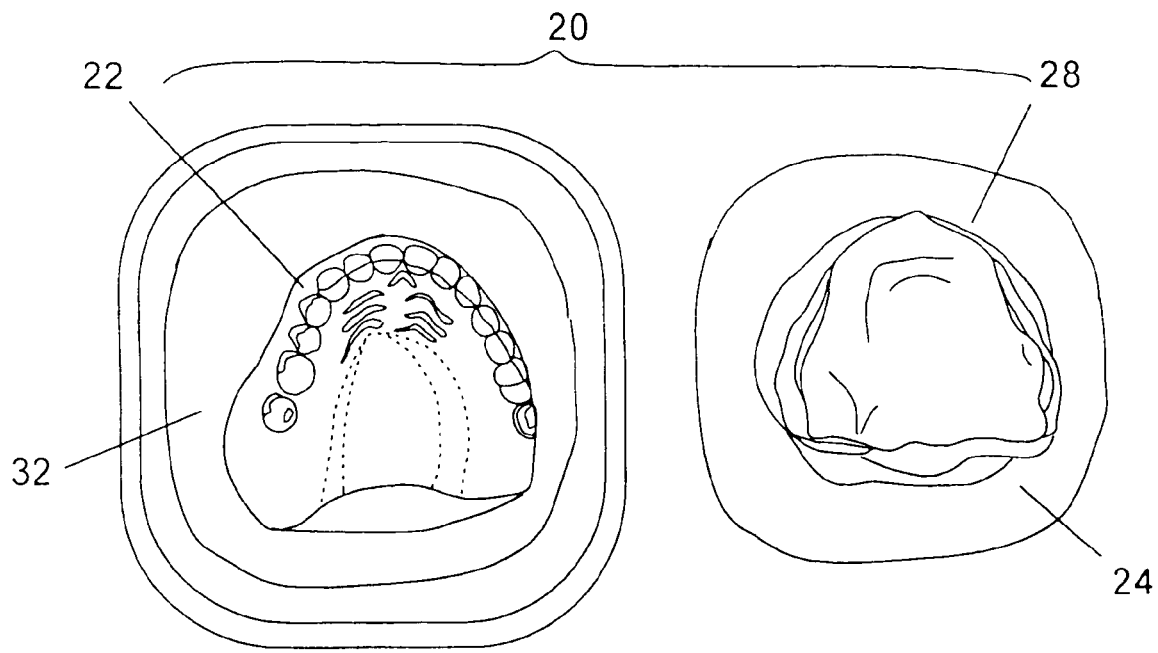
FIG. 8 is a view of the two mold sections.
Figure 9:
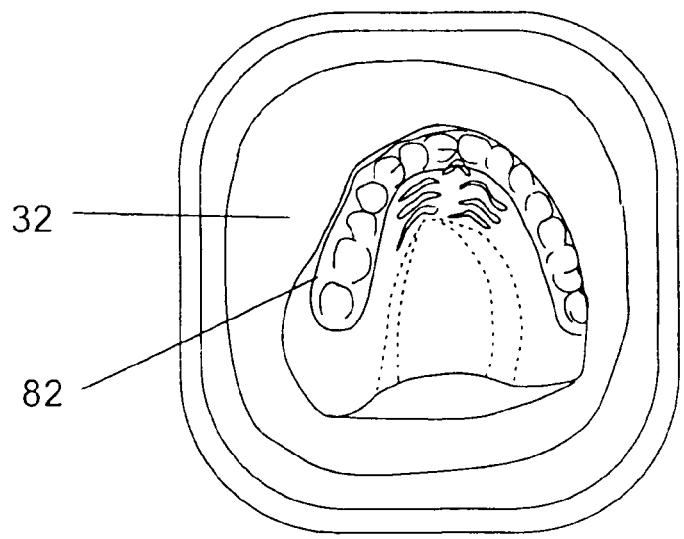
FIG. 9 is a view showing the step in which a denture material, having a white pigment, is poured into the bottom portion of the mold to form the teeth.

FIG. 7 shows the interior of the resilient second mold section 32. The teeth mold portion 34 is an impression of the exterior surfaces of the teeth 8 in the original denture 2 so that the exterior shape of the original teeth can be duplicated in the mold. The gum mold portion 36 also conforms to all exterior surfaces of the gum 10 in the original denture 2. The mold gum line 38 also will conform to the gum line 12 in the original denture 2.

Figure 6:
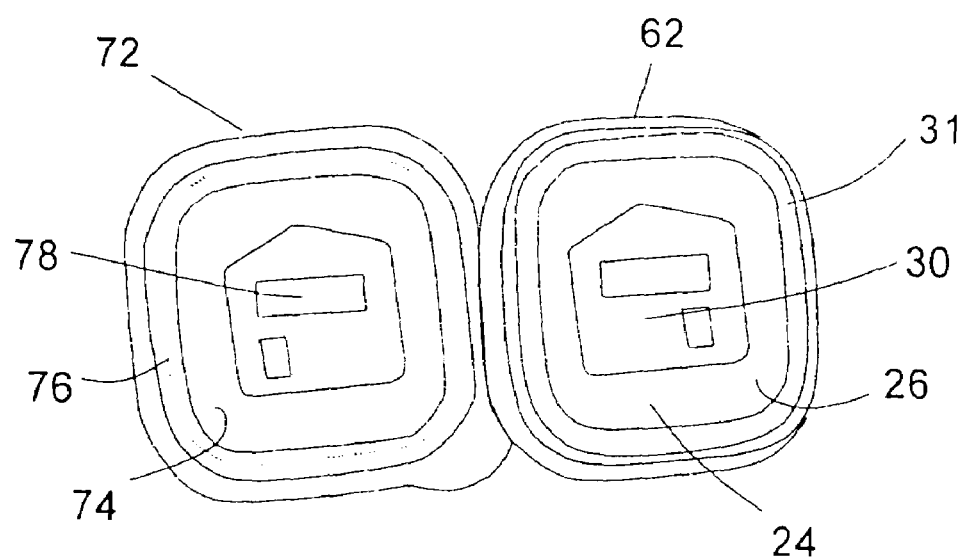
FIG. 6 is a view of the inside surface of the dental flask lid and the outer surface of the tissue side mold section. Registration indicia on both the lid and the tissue side mold section surface are shown.

After both the tissue side mold section 24 has solidified to form a first solid member and the second mold portion 32 has solidified to form the second solid mold member, the original denture 2 can be removed from the mold 20 leaving a mold cavity 22 that will conform almost exactly to the outer periphery of the original denture 2. Removal of the original denture is accomplished by first removing the lid 72 from the dental flask 60, as shown in FIG. 6. The first mold section 24 can then be moved transversely to the open end of the dental flask 60 to remove the tissue side mold section 24 from the dental flask 60 and to separate the tissue side mold section 24 from the original denture 2. Since the relatively rigid dental stone mold section 24 conforms only to a surface of the denture without undercuts, this rigid mold section 24 can be easily removed without damaging the original denture 2. The relatively more flexible exterior side mold section 32 can now be flexed around the original denture 2 to free that denture from the mold 20. The fabrication of entire mold 20, and removal of the original denture can be accomplished by a dental technician in the relatively short time. Although the mold 20 could be immediately used to fabricate a duplicate denture, it could also be stored for a long period of time until the original denture 2 is lost or damaged. Since the tissue side mold section 24 is fabricated from dental stone or a similar material, its dimensions will not change with time. The mold 20 can then be used many years later to provide the denture wearer with a duplicate denture with the same shape as the original denture 2. Dentures are often lost by elderly patients, who can no longer assist a dentist during fitting of a new denture. This mold 20 can be used to fabricate a replacement, without the otherwise necessary cooperation of the denture wearer. Even if the denture wearer can help the dentist to fit and prepare a new denture, that process takes a considerable time and a replacement denture can be provided within two days or less from the time the original denture is reported to have been lost or damaged. The mold 20 can be stored or retained by the dentist who fabricates the original denture, or who constructs the mold to match an existing denture. There is no theoretical reason why the mold cannot be kept by the denture owner. However, the mold can also be stored at a central location, such as a laboratory serving a particular area or an entire country. A central lab of this type would have the facilities to store molds 20 under climate controlled conditions, and the central lab would have equipment, supplies, and trained personnel to efficiently fabricate a duplicate denture on short notice.

The mold 20 can be used to fabricate a new denture using standard dental resins, such as methylmethacrylate. According to the preferred embodiment of this invention, both the duplicate denture teeth and the duplicate denture gum will be formed from the same resin. In this instance the new denture will differ from the original denture in which teeth are typically formed using a material different from the material used to form the gum portion. However, this duplicate denture is intended to be either an inexpensive substitute for an original denture, or to be a short term substitute until a new conventional denture can be fabricated. Of course a different material can be used to form the duplicate denture teeth and gum portions if desired.

One step can occur either at the time of original fabrication of the mold 20 or at the time that a duplicate denture 80 is to be fabricated. An injection passage 44 is drilled from the exterior of the flask 60 into the mold cavity 22. In the preferred embodiment, this injection passage intersects the mold cavity 22 in the central portion 40 of the exterior mold section 32. At least one overflow passage is also drilled through the resilient material forming the exterior mold section 32. In the preferred embodiment, two overflow passages 46, 48 are drilled through flanking portions 42 on both sides of the central mold portion 40.

Figure 10:
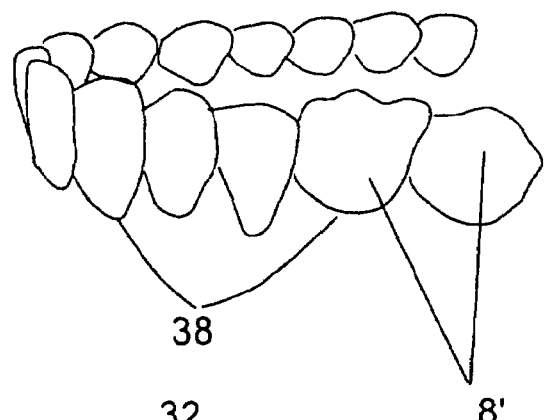
FIG. 10 is a view of the teeth, formed in the step shown in FIG. 9, after solidification and removal from the bottom portion of the mold so that this one piece replication of the exterior surfaces of the teeth can be trimmed along the gum line.
Figure 11:
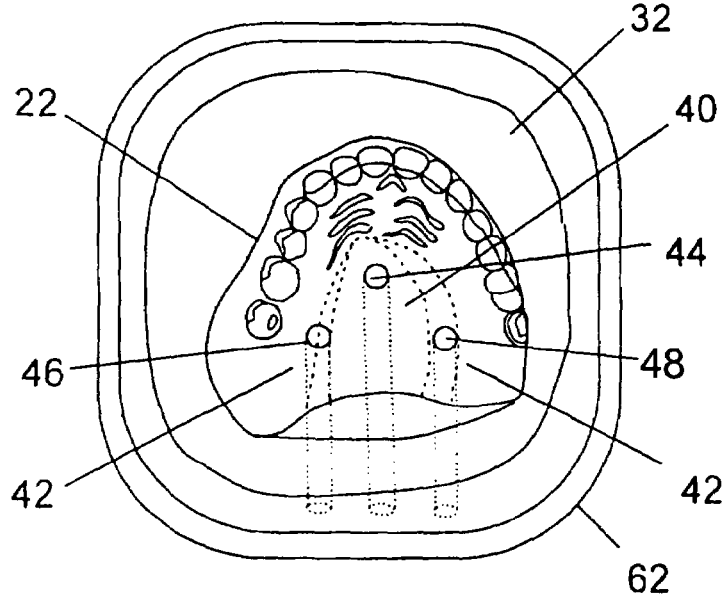
FIG. 11 is a view showing the bottom portion of the mold, with the trimmed teeth reinserted into this portion of the mold, and with holes drilled into the bottom portion of the mold so that denture material can be injected to form the gum portion of the duplicate denture.
Figure 12:
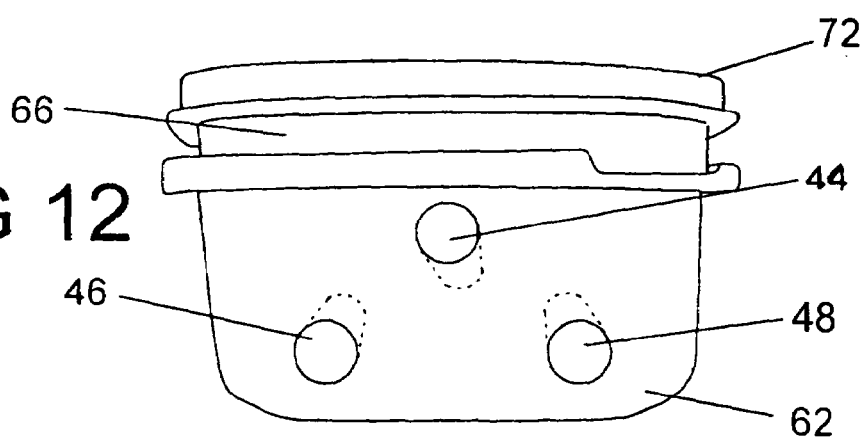
FIG. 12 is a view showing injection of denture material in a liquid form into the mold including the tissue side mold and the bottom portion of the mold, with the duplicate teeth in place in the mold, so that the gum portion of the duplicate denture can be fabricated.

In the preferred embodiment of this invention, the duplicate denture teeth are fabricated prior to fabrication of the duplicate denture gum portion. The tissue side mold section 24 and the flask lid 72 are first removed, exposing the portion of the mold cavity 22 formed by the exterior side mold section 32. Liquid methylmethacrylate resin, including a white pigment, can be poured into the portion of the mold cavity 22 that conforms to the periphery of the teeth. This portion of the mold cavity 22 is completely defined in the exterior side mold section 32, which is mounted in the dental flask base 62. A sufficient quantity of white pigmented methylmethacrylate liquid 50 is poured into the mold section 32, until the mold cavity 22 is filed above the gum line 38. At this point, the resin is cured by conventional means so that it solidifies. As shown in FIG. 10, this solid teeth segment 82 is removed from the mold cavity 22, by flexing the resilient material forming mold section 32 if necessary, as a single piece. This one piece teeth segment is then trimmed along the gum line, which is clearly identifiable because of the impression of the gum line 38 formed in mold section 32. The individual teeth are not separated when the teeth segment is trimmed. The trimming step is merely intended to shape this portion of the duplicate denture so that it will have the appearance and white color of the teeth 8 in the original denture 2. After the unitary teeth segment 82 has been trimmed, it is reinserted into the resilient exterior side mold 32.

The tissue side mold section 24 can now be reinserted into mating relationship with the exterior side mold section 32. Since the exterior side mold section 32 was originally formed with areas mating with the tissue side mold section 24, these two mold sections can be at least approximately realigned. The resiliency of the exterior mold section facilitates this realignment in which the shape of the mold cavity at least closely approximates the shape of the original denture. The registration indicia 30 on the tissue side mold section 24, and the companion registration indicia 78 on the inner surface 74 of the lid 72 provide a means for even more precise alignment of the mold sections 24, 32 so that the mold cavity 22 will have a shape that closely duplicates the shape of the original denture 2. When the lid 72 is mounted on the base 62, as the lip 66 enters the lid groove 72, the registration media 30 on the lid 72 will result in proper alignment of the tissue side mold section 24 relative to the dental flask 60 and the exterior side mold section 32 housed in the dental flask 60.

At this point, the gum segment 84 of the duplicate denture 80 can be fabricated by injecting a second liquid resin 52 through the injection passage 44 into the mold cavity 22. In the preferred embodiment this second liquid resin comprises methylmethacrylate with a pink pigment suspended therein. By using methylmethacrylate to form both the teeth segment 82 and the gum segment 84 of the duplicate denture 80 a good bond at the interface between the two segments 82, 84 will be assured even though the teeth segment has previously cured or solidified. To insure that the mold cavity 22 is completely filled, the second liquid resin is injected through the injection passage 44 until excess resin exits the flask 60 through both overflow passages 46, 48. This configuration not only insures that the mold cavity 22 is initially completely filled, but the injection passage 44 and the overflow passages 46, 48 serve as reservoirs of resin so that voids are not formed in the mold cavity 22 or in the gum segment 84 as the second resin 52 solidifies. No dental presses are therefore required to form both segments of the duplicate denture, because excess material is available to form both segments. After the second resin solidifies, the lid 72 and the tissue side mold section 24 are removed and the solid material is trimmed at the intersection of the injection passage 44 and the overflow passages 46, 48 and the mold cavity 22. The duplicate denture 80 can then be removed from the exterior side mold section 32 and the dental flask 60. At this point the duplicate denture 80 can be trimmed and smoothed and is then substantially ready for use by the denture wearer. Of course a dentist should make minor modifications to the duplicate denture at this point so that it will be suitable for use by the denture wearer.

A mold fabricated in accordance with the preferred embodiment can also be used with methods or techniques for filling that mold other than the preferred method disclosed herein. The method of injecting material can also be used with molds that may differ in one or more aspects from the mold described herein. This method is applicable to both upper and lower dentures and can be employed in the fabrication of partial dentures.

Different materials can be used for the part of the mold and for molding or casting the denture. Dental stone does provide a dimensionally stable mold material for subsequently reproducing the tissue side of a denture, but this relatively rigid and brittle material may cause problems when relatively inexperienced technicians attempt to use dental stone to fabricate a denture mold. Potential damage to the denture makes dental stone a less than optimum material. Certain addition-cured silicone rubbers, such as REDU-IT silicone rubber duplicating material available from American Dental Supply, Inc., do not exhibit unacceptable shrinkage, and a second embodiment of this invention permits the use of addition-cured silicone rubber to form a mold including a tissue side mold 124 and an exterior side mold 132 for fabricating a replacement denture 2'. The flexibility of an addition-cured silicone rubber facilitates removal of the original denture 2 after the two halves of the mold have set, but the dimensional stability of addition-cured silicone rubber results in a properly fitting replacement denture 2'.

Addition-cured silicone rubbers are formed by mixing two reactive materials. When these materials are first mixed, the resulting composition is in the form of a fluid, which after a suitable curing time takes on a permanent set as an elastomeric material. A two part mold cannot be formed by placing an original denture 2 in a dental flask 160 or container and pouring the fluid silicone rubber composition the denture to embed it. First it would be impossible to suspend the original denture 2 in the dental flask 160 so that the addition-cured silicone rubber would surround all of the surfaces of the original denture 2. Even if it were possible to pour the fluid silicone rubber composition into the flask 160 so that it would embed all critical surfaces, the one-piece silicone rubber mold would have to be cut into at least two separate parts in order to remove the embedded original denture 2. Even if the silicone rubber mold could be cut after the material has taken on a permanent set, there would still be an unacceptable possibility that the original denture 2 would be damaged. It would also be difficult to separate the two flexible mold halves along a parting surface that would facilitate efficient removal of either the original or the duplicate denture from the two part mold.

Figure 13:
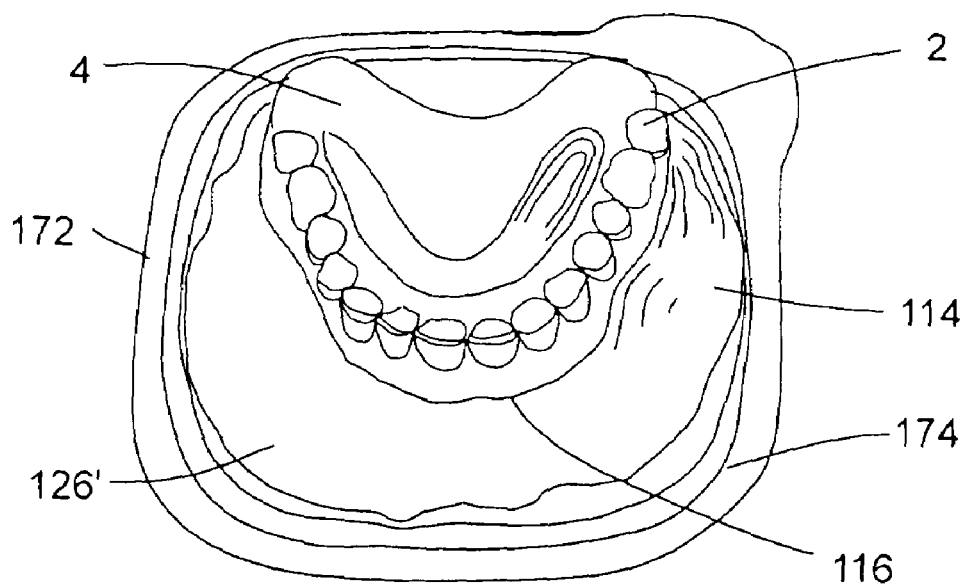
FIGS. 13–19 describe an alternate method and apparatus for fabricating a mold to duplicate a denture.

In accordance with the embodiment of this invention depicted in FIGS. 13–19, two flexible mold parts 124, 132 are formed in a multi-step process. In the first step of this process, the tissue side 4 of the original denture 2 is covered by a malleable or pliable sacrificial or filler material 114'. The resultant temporary or sacrificial member 114 partially fills a portion of a dental flask 160 so that the remaining portion of the flask can be filled with a fluid material 132' to form a first part 132 of the multi-piece mold. It is not necessary that this sacrificial or temporary filler member 114 conform precisely to the contour of the tissue side 4 original denture 2. It is only important that this or temporary sacrificial member 114 cover those surfaces on the original denture that will be matched by a subsequently formed tissue side mold member 124. A simple material such as play dough, formed by combining flour, vegetable oil, salt and boiling water in a conventional manner can be used to form this sacrificial member 114. This sacrificial member 114 is formed on one of the two parts of the flask or of the container 160 in which the mold is to be formed. Two alternative methods of forming this sacrificial member will be subsequently discussed. As shown in FIG. 13, filler material 114 covers the tissue side 4 of original denture 2 substantially up to a parting line 116 along the original denture 2, which will separate the denture tissue side 4 from the denture exterior side 6. Of course a complementary parting line will be eventually formed on the two mold parts. A diverging, sloping surface 126' extending away from this parting line 116 and away from the original denture 2, should also be formed on the sacrificial member 114. This diverging, sloping surface 126' extends completely around the sacrificial member 114. The sacrificial member 114 will then comprise a male member, and the significance of the sloping surface 126' will be subsequently discussed with reference to the positioning of the two mold halves 124, 132 and to the storage of the two mold halves in an unloaded condition in which the two elastomeric mold parts will not be subject to forces that might cause creep or result in cold deformation.

In the embodiment shown in FIGS. 13–19, the sacrificial member 114 covers the tissue side 4 of the original denture 2 and is mounted on the dental flask cover or lid 172. One technique for forming this temporary sacrificial member is to apply the malleable filler material 114A to the tissue side of the denture and filler material 114B the inner face 174 of the dental flask cover 172 in a process commonly referred to as "cow piling". The cover 172 and the original denture 2 are then joined as temporary subassembly by pressing the two masses of sacrificial material 114A, 114B together and shaping the exterior of the temporary sacrificial member 114 into a smooth surface. This exterior smooth surface should be tapered away from the denture 2 to form a diverging sloping surface 126' which extends from the eventual mold parting line 116 toward the edge of flask cover 172. A release agent is applied to the exposed surfaces of the original denture 2 and to the exposed surface of the sacrificial or temporary filler member 114.

Figure 14:
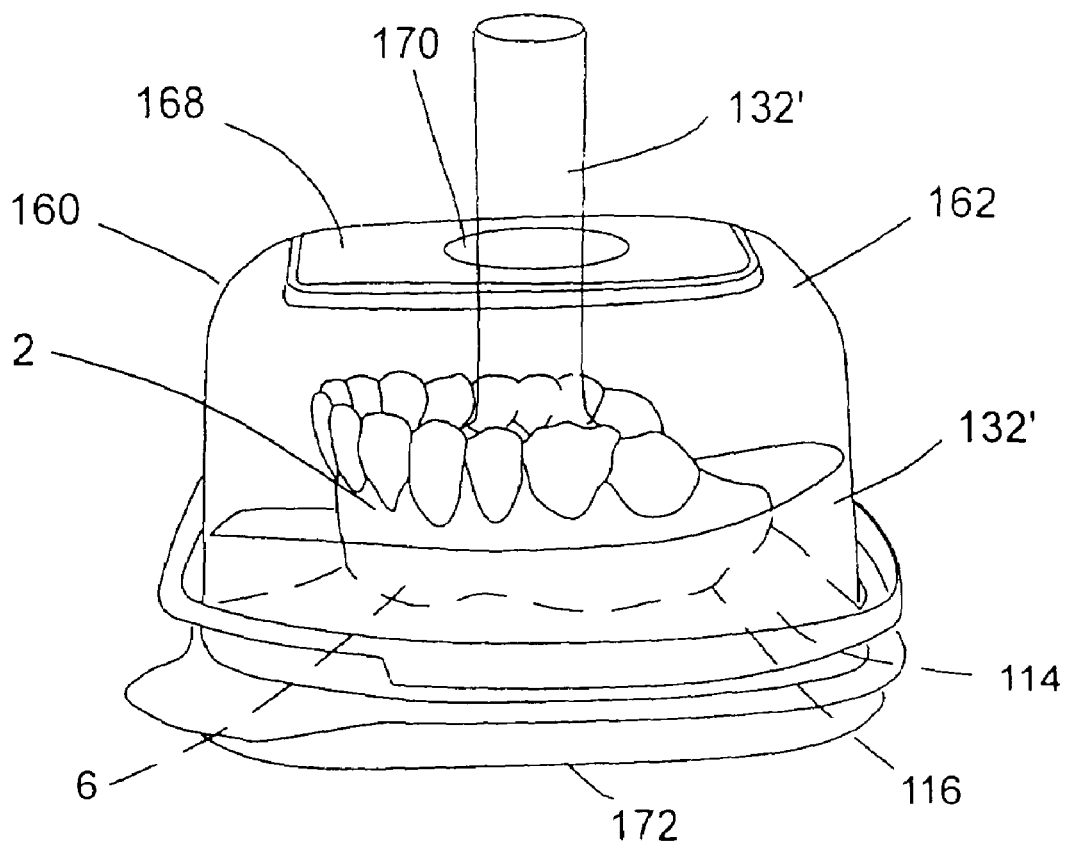
Figure 15:
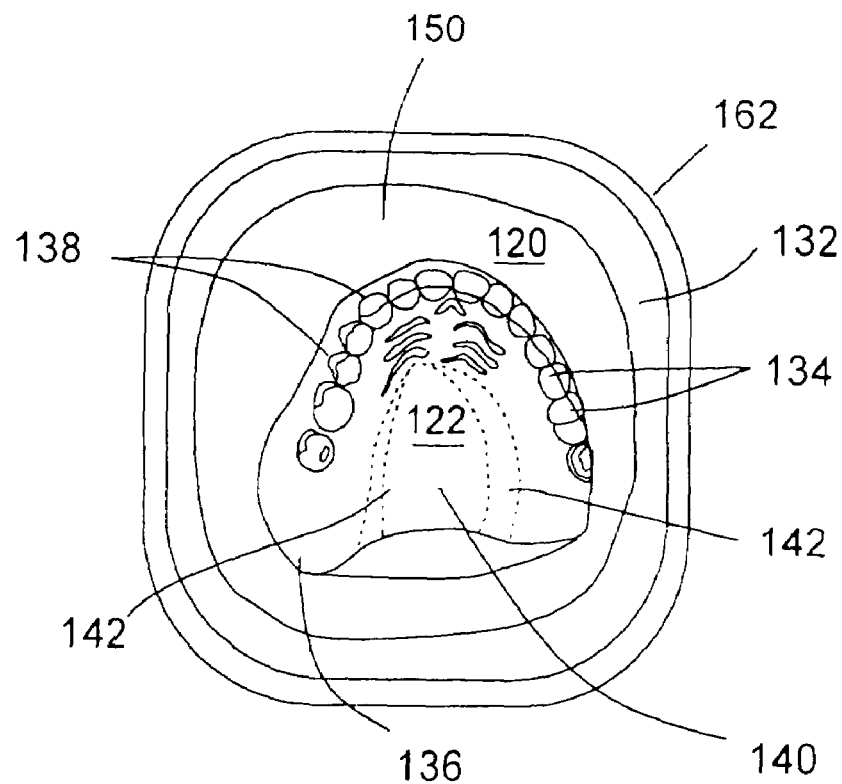
Figure 16:
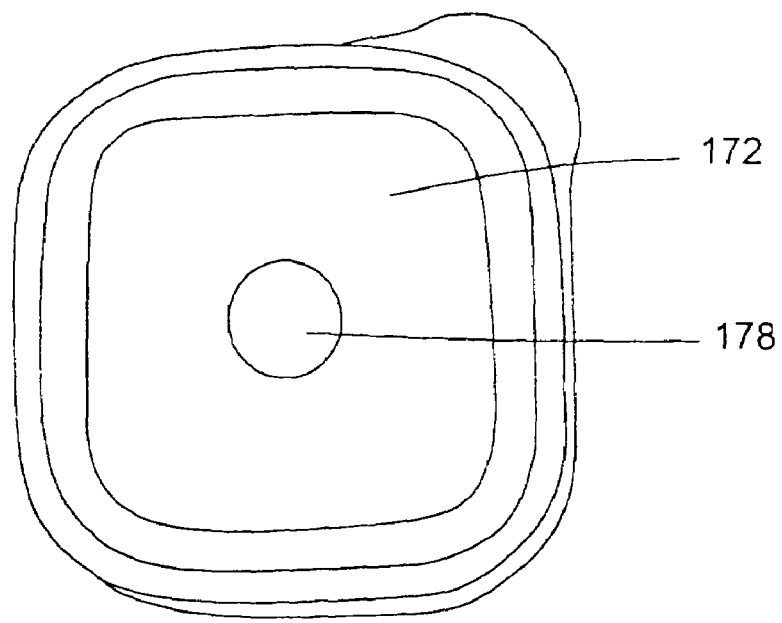
Figure 17:
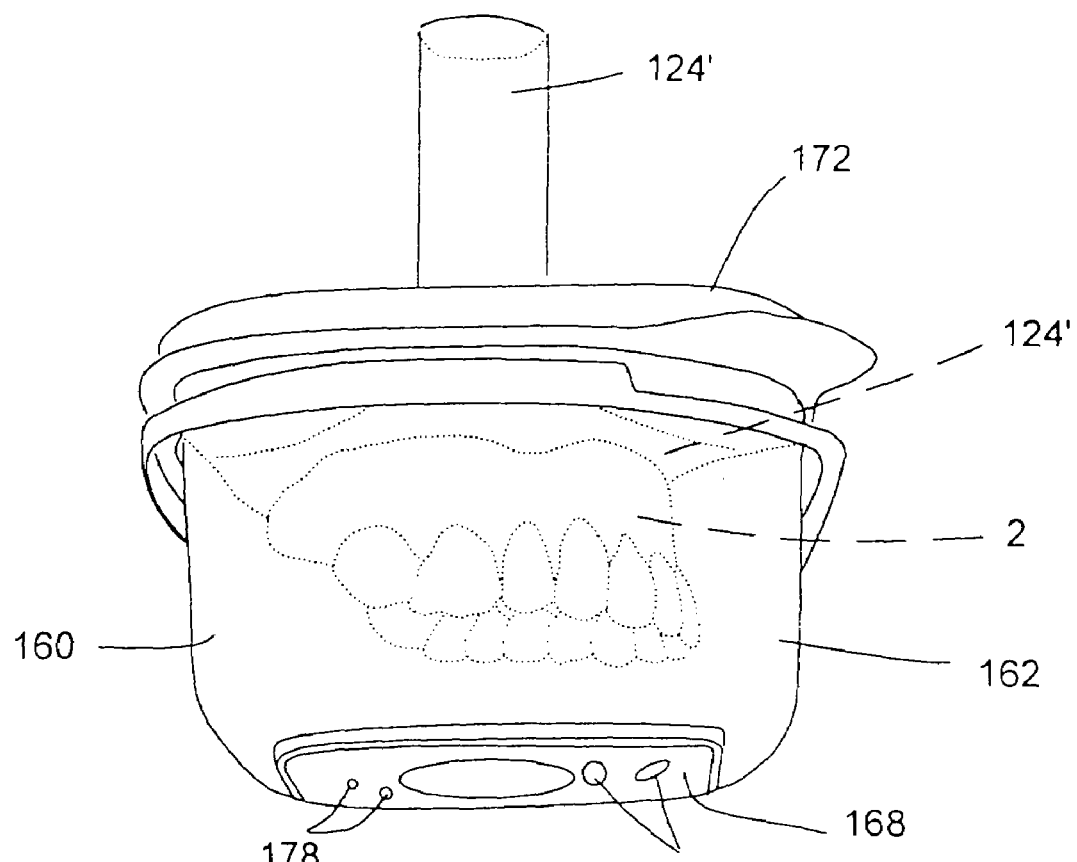
Figure 18:
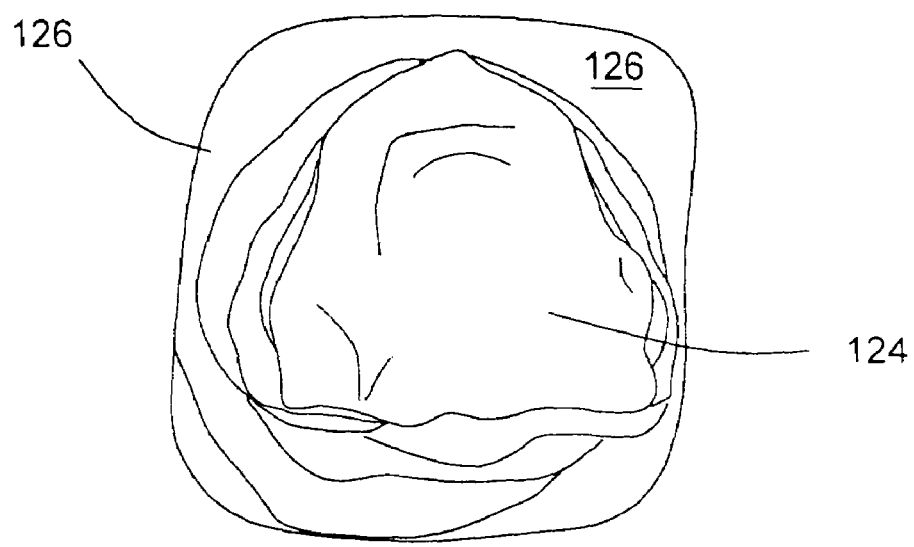
Figure 19:
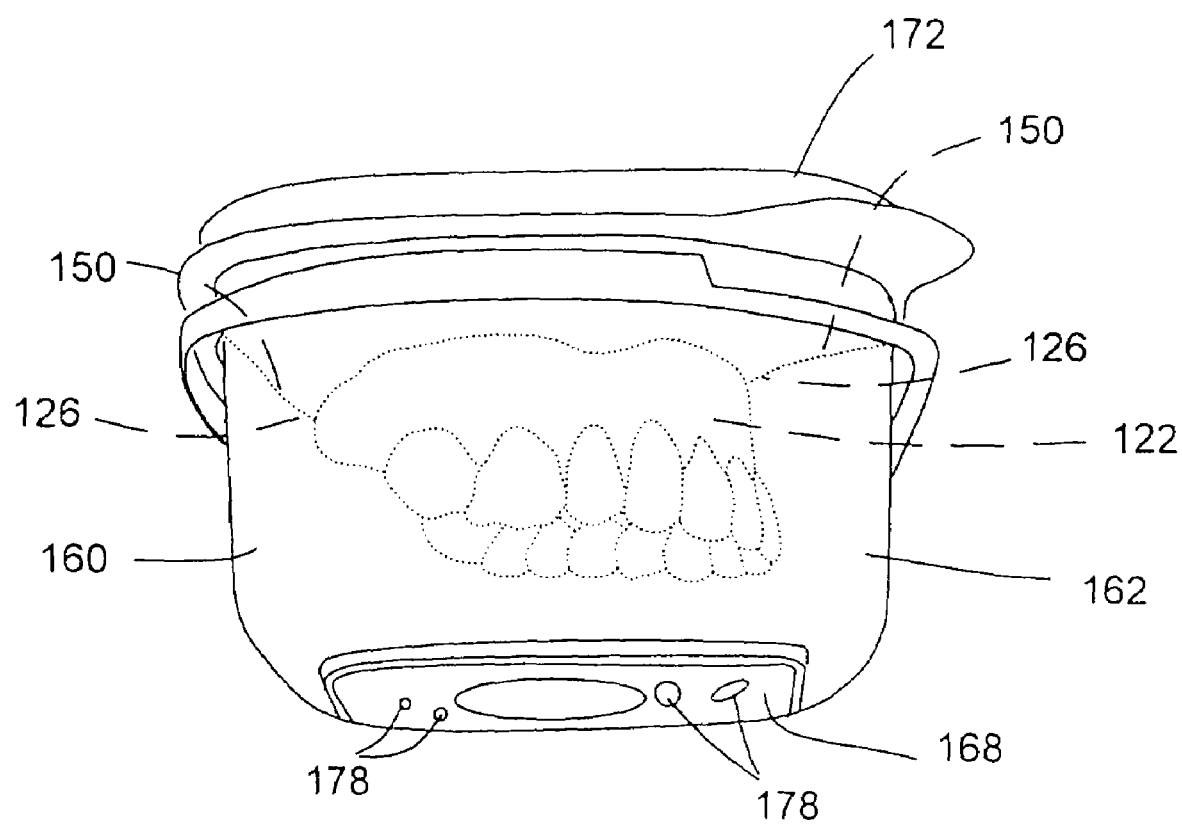

The temporary subassembly including the original denture 2, with the formable sacrificial material covering the tissue side 4 of the original denture 2, and the flask cover 172 is then mated to the flask base 162. The flask base 162 has a hole 170 in the face 168 opposite from the flask base open face on which the flask cover 172 is mounted. As shown in the embodiment of FIG. 14, this hole 170 is centrally located and extends into the flask base 162. With the original denture 2 positioned within the dental flask 160 in this manner, fluid addition-cured silicone rubber 132' will be poured into the dental flask container 160 through the hole 170 in the bottom surface 168. The dental flask 160 will be filled and a small amount of fluid addition-cured silicone rubber 132' may be allowed to overflow the flask 160. The fluid silicone rubber 132' will then be allowed to cure and take on a permanent set by placing the dental flask 160 in an upside down position with the bottom face 168 of the flask base 162 in an elevated position. This will allow any air bubbles or voids to rise as the material cures and solidifies, so that any voids or irregularities 178 will be formed along the bottom surface 168 of the flask 160 and away from the original denture 2 and from the mold cavity 122 to be formed by the two mold halves 124, 132 (See FIG. 19). By allowing the silicone rubber to cure in this manner, the contour of the mold cavity 122 will be formed without any significant voids or irregularities along the mold cavity surface formed where the silicone rubber conforms to the exterior side of the original denture 2. It should be understood that while addition-cured silicone rubber is used to form the exterior mold side 132 in this embodiment of the invention, other materials having less dimensional stability can be used to form the exterior side mold half 132, if desired. The dimensions of exterior side of the replacement or duplicate denture will not be as critical as the dimensions and surface character of the tissue side 124 of the replacement or duplicate denture 2'.

After the exterior side mold half 132 has taken on a permanent, if flexible set, the original denture 2 and the sacrificial member 114 will removed from the dental flask base 162 and separated from the exterior side mold half 132. The sacrificial member 114 will then be removed from the original denture 2 and from the flask cover 172 and can be discarded. Preferably the material used to form the sacrificial member 114 will have a distinct color that differs from the color of the original denture 2 and from the material used to form the exterior side mold part 132. Any flakes or other residue can then be removed from original denture 2 and from the parting surface 150 formed on the exterior side mold part 132. The use of a flour based play dough material has two advantages. First a simple food coloring can be used to impart the distinctive material to the play dough material. Second this material will leave no harmful residue on the original denture.

The tissue side mold 124 can now be formed using an addition-cured silicone rubber. First the original denture 2 is repositioned in the exterior side mold part 132, which has now taken on a permanent, resilient shape. The elasticity of the exterior side mold 132 will permit insertion of the original denture 2 back into position without any damage to the original denture 2 or to the exterior side mold part 132. A mold release agent is applied to the tissue side of the original denture 2, and to the exposed surface of the exterior side mold part 132. Next, the cover 172 is again mounted to the flask mold base 162. The flask cover 172 has a central opening 178 through which fluid addition-cured silicone rubber material 124" can be poured to form the second or tissue side mold part 124. Note that the central opening 178 in the flask cover 172 can be drilled, formed or cut into the flask cover 172 either before or after use of the flask cover 172 to mount the temporary sacrificial member 114. Typically the sacrificial material used in the previous step will be sufficiently viscous so that the existence of a central hole 178 in the flask cover 172 will not be a problem. Alternatively, separate flask covers, one with a central opening and one without a central opening can be used in the two steps.

The fluid addition-cured silicone rubber material 124' poured through the flask central opening 178 will conform precisely to the tissue surface of the original denture 2. The fluid addition-cured silicone rubber material 124' will not react with those portions of the solidified exterior side mold part 132 with which the fluid material 124' comes into contact, even though the two mold parts will essentially have the same chemical composition. The dental flask 160 will be filled and fluid addition-cured silicone rubber may be allowed to overflow through the central opening 178. The fluid addition-cured silicone rubber 124' will then be allowed to cure and solidify in substantially the same manner in which the exterior side mold part 132 was formed. The flask 160 will remain in an upright position while the tissue side mold part 124 solidifies as the addition-cured silicone rubber sets. Again an air bubbles will rise away from the surface of the mold cavity 122 to be formed along the contour of the original denture. Voids will therefore be formed adjacent to the flask cover and away from the mold cavity insuring a conformal tissue mold surface.

After the tissue side mold 124 has solidified into a resilient member, the flask cover 172 will be removed and the tissue side mold 124 can be separated from the original denture 2 and the exterior side mold 132 and removed. The original denture 2 can then be extracted. When the two mold parts 124, 132 are then mated, a mold cavity 122 having the shape of the original denture, including the teeth and gum sections, will be formed. A parting line 116 substantially following the juncture of the denture tissue side 4 and the denture exterior side 6 will be formed on the two mold halves 124, 132. Minimal overlaps will be present in either mold half, and the resilient and flexible character of the solidified addition-cured silicone rubber will allow extraction of either the original denture 2 or of replacement dentures 2' formed in this resilient mold.

Two mating sloping surfaces 126, 150 will be formed on the tissue side mold part 124 and the exterior side mold part 132. These sloping surfaces 126, 150 will extend from the parting line 116 away from the mold cavity 122. On the tissue side mold part 124, this sloping surface 126 will diverge. On the exterior side mold part 132, the sloping surface 150 will converge. These sloping surfaces 126, 150 will then accurately position the upper tissue side mold part 124, both vertically and laterally, relative to the lower exterior side mold part 132 when the upper tissue side mold part 124 is inserted into the dental flask 160. When these two sloping surfaces 126, 150 are mutually registered, a mold cavity 122, having the same shape as the original denture 2, will be formed between the two mold parts 124, 132. These sloping surfaces 126, 150 will define a relatively large bearing surface on which the upper tissue side mold 124 will rest even though the two mold parts 124, 132 are resilient. Any mating pressure will be born be surfaces 126, 150 beyond the mold cavity 122 so that there will be no deformation of the mold cavity 122. Thus the mold cavity 122 will not be deformed when material is injected into the mold cavity 122, through one or both of the mold parts 124, 132, to form the replacement denture 2'. Also the support provided by the upwardly facing lower mold surface 150 will not result in any significant loads that would tend to cause deformation or creep while the two mold parts 124, 150 are in storage. Furthermore, any clamping force applied when the flask top 172 is mounted on the flask base 160, will not cause permanent deformation of the mold parts in a manner that would result in dimensional changes to the mold cavity 122.

Figure 20:
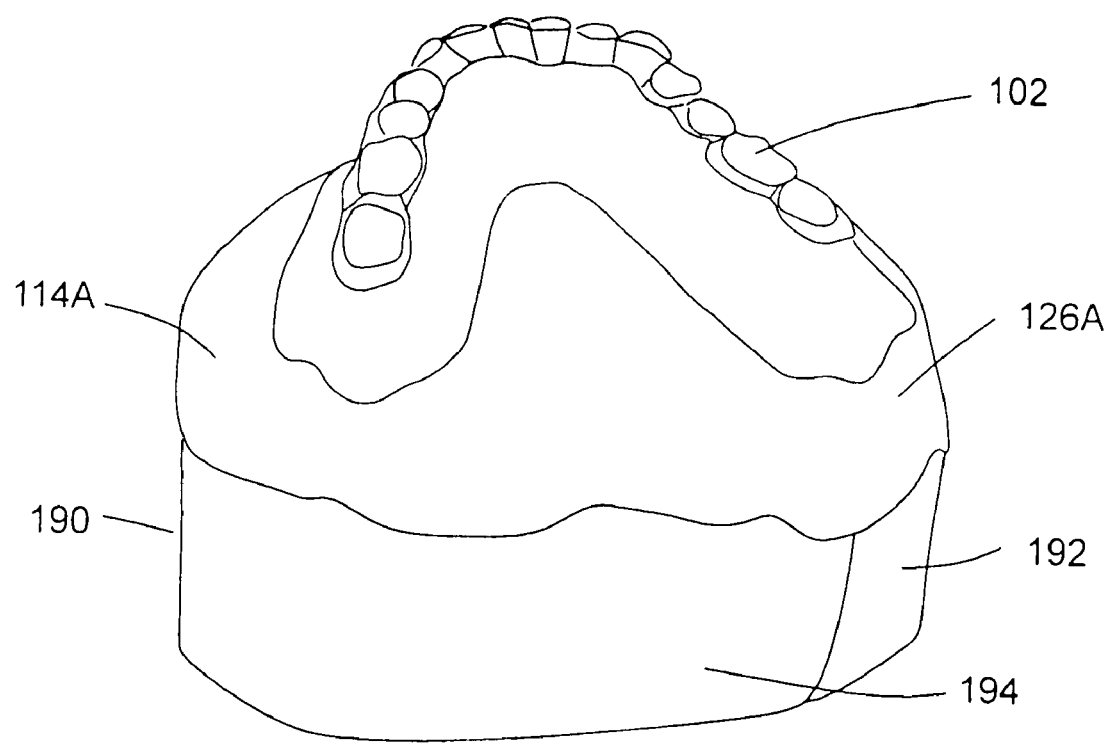
FIGS. 20 and 21 show a third embodiment of the apparatus and method for fabricating the mold.
Figure 21:
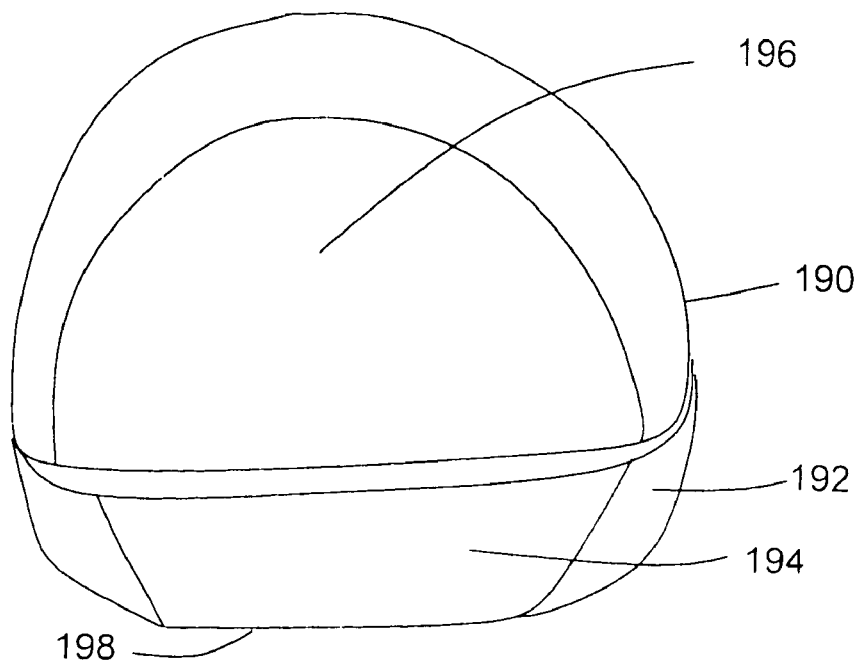

In the embodiment of FIGS. 13–19, the shape of the sloping surfaces on the two mold parts is dependent upon the manner in which the technician originally forms the tapered surface on the sacrificial member, which covers the tissue side of the original denture. FIGS. 20 and 21 show an alternate manner in which this sloping surface is formed. In this embodiment, a tray 190, with inclined outer surfaces 192, 194, is used to form a portion of the temporary dam, which fills part of the dental flask 160 as the exterior side mold part 132 is poured and cured. The inclined exterior sides 192, 194 on the tray taper inwardly from a wider base 198, which is mounted on the inner face of the flask cover 172. The tray 190 has a central compartment 196 in which sacrificial or filler material 114 can be mounded so that the entire outer surface of the sacrificial material 114 and the tray in which it is contained is convex or forms a male protrusion or mound. The original denture 102, shown here as a mandibular denture, can then be pressed into the sacrificial material 114 in the tray, to cover the tissue side of the denture 102. The malleable sacrificial material 114 can then be smoothed so that the exterior surface of this dam assembly will be sloping or diverging from the location of the original denture 102 toward the base 198 of the tray 190 and the flask cover 170. This assembly can then be mounted in the dental flask 160 in the same manner as the previous embodiment and the remainder of the flask 160 can be filled to form the opposite part 132 of the mold. When the dam assembly is removed, the tray 190 can be reused by refilling the central compartment 196 with sacrificial material or by reusing salvaged malleable material. This tray 190 simplifies the work of the technician and helps insure that a smooth sloping parting surface will be formed between the two resilient mold parts. This tray can also be fabricated as part of the flask cover used to close the flask when the first or exterior side mold part is poured. A different flask cover would then be used for fabrication of the tissue side mold.

In the preferred embodiments of this invention, the tissue side mold part is located on the flask cover side of the mold and the exterior side mold part is located in the flask base. The relative orientations of the two parts of the mold can be reversed, but it has been found that extraction of the original denture and of the replacement denture is easier if the tissue side mold part is located on the top. Otherwise the mold cavity may be situated too deeply within the mold flask base, making it more difficult to extract dentures form the mold cavity.

For each of the various methods of fabricating a mold for manufacturing replacement dentures, the denture mold cavity can be filled using the procedure described with reference to FIGS. 9–12.

The apparatus and method according to this invention have been described in terms of a representative and preferred embodiments. However, the invention as defined by the following claims is applicable not only to the representative embodiments depicted herein, but also to other embodiments of the methods and apparatus as claimed, which would be apparent to one of ordinary skill in the art. For example, the flask cover and the flask base can be joined by a flexible hinge, and the tissue side mold part and the exterior side mold part can be fabricated in the same manner and used to fabricate the replacement denture in the same manner.

We claim:

1. A mold for fabricating a duplicate for an original denture, the mold including:
   a flask;
   a first flexible mold section;
   a second flexible mold section located within the flask, the first and second flexible mold sections forming at least part of a denture mold cavity in which the duplicate of the original denture is molded;
   wherein, the first and second flexible mold sections include sloping surfaces, each formed upon solidification of an initially fluent material, extending away from the mold cavity, the sloping surfaces being conformable to each other and mutually registerable and comprising means for aligning the first and second flexible mold sections to form the denture mold cavity.

2. The mold of claim 1 including a flask in which the first and second mold sections are positioned.

3. The mold of claim 2 wherein the second mold section comprises a mold base located in a flask base, the first mold section being removable from the flask to expose the mold cavity.

4. The mold of claim 1 wherein the first mold section comprises a tissue side mold section and the second mold section comprises an exterior side mold section forming the exterior contour of denture teeth and the denture gum section.

5. The mold of claim 1 wherein the first and second sloping surfaces comprise means for laterally aligning the first and second flexible mold sections without subjecting the first and second mold sections to loads which deform the mold cavity.

6. A mold for fabricating a substitute denture having the same external shape as an original denture, the mold comprising:
   a first mold section;
   a second mold section;
   a denture mold cavity, conforming to the external shape of the original denture and defined at least in part by the first and second mold sections formed around the original denture, the first and second mold sections having surfaces, each formed upon solidification of an initially fluent material, extending away from the denture mold cavity, the molded surfaces on the first and second sections being conformable so as to be matable when the first and second mold sections are positioned together to form the denture cavity, the first and second mold sections being formed so that the original denture can be removed from the denture mold cavity;
   a mold flask including a first flask section matable with a second flask section;
   the mold being characterized in that the first mold section is located within the first flask section and the second mold section is in engagement with the second flask section;
   wherein an exterior surface on the first flask section includes an opening through which fluent material can be injected, when the first flask section is mated to the second flask section, to solidify in the first flask section to form a flexible portion of the mold cavity comprising part of the first mold section;
   and wherein, the flask comprises a container for storing the first and second mold sections without applying loads to the first and second mold sections so that the mold remains dimensionally stable and the mold can be stored in the mold flask for use in fabricating the substitute denture upon loss of, or damage to the original denture.

7. The mold of claim 6 wherein the second flask section includes a second opening in a second exterior flask surface through which fluent material can be injected to solidify in the second flask section to form the second mold section.

8. The mold of claim 6 wherein voids in the first and second mold sections are concentrated adjacent exterior flask surfaces through which fluent material can be injected and away from the denture mold cavity so that the mold cavity is defined by relatively smoother surface contours.

9. The mold of claim 6 wherein the first mold section comprises an exterior side mold section and the second mold section comprises a tissue side mold section having a contour conforming to a tissue side of a denture to be fabricated in the mold cavity.

10. The mold of claim 6 wherein the first flask section comprises a base and the second flask section comprises a cover attachable to the base, the volume of the base being sufficient to house the first and second mold sections and the denture mold cavity.

11. The mold of claim 6 wherein both the first and second mold sections comprise flexible mold sections.

12. The mold of claim 6 wherein the first and second mold sections include first and second sloping surfaces extending away from the mold cavity, so that opposing first and second sloping surfaces fit together in mutual registration to align the first and second mold sections to form the denture mold cavity.

13. The mold of claim 12 wherein the first and second sloping surfaces comprise means for laterally aligning first and second flexible mold sections without subjecting the first and second mold sections to loads which deform the mold cavity.

14. A kit for fabricating a mold for using in duplicating an original denture, the kit including:
   a flask comprising a base and a cover
   the kit being characterized by an opening in at least one of the base or the cover through which a fluent material can be poured when the base and cover are mated;
   a material conformable to one surface on a portion of an original denture to form a solid temporary filler for supporting the original denture in the flask; and
   a fluent material solidifiable after being poured into the flask through the opening and comprising means for forming a flexible portion of a mold cavity conforming to a portion of the original denture located in the flask.

15. The kit of claim 14 wherein the solid material comprises a malleable material removable from the flask after the fluent material solidifies to form a first mold section, and the other of the base and cover also includes an opening though which fluent material can be poured to form a second mold section in the space vacated by removable of the malleable material.

* * * * *